United States Patent [19]

Price

[11] Patent Number: Plant 7,228

[45] Date of Patent: May 15, 1990

[54] PECAN TREE (PRICE-FLEMING)

[76] Inventor: Jack W. Price, Rte. 3, Box 161, Rocky Mount, N.C. 27804

[21] Appl. No.: 323,611

[22] Filed: Feb. 9, 1989

[51] Int. Cl.[5] ..... A01H 5/00

[52] U.S. Cl. ..... Plt./31

[58] Field of Search ..... Plt. 31

[56] References Cited

U.S. PATENT DOCUMENTS

P.P. 510 4/1942 Harris ..... Plt. 31

P.P. 5,911 3/1987 McDowell ..... Plt. 31

OTHER PUBLICATIONS

Pecan South, Sep.–Oct., 1988, (excerpt).

*Primary Examiner*—Howard J. Locker

[57] ABSTRACT

A pecan tree designated "Price-Fleming" is a new and distinct variety of pecan tree distinguished by a high quality crop of large, very tasteful, thin shelled nuts with light golden meats. The fruit ripens mid October to mid November. The early maturity of the nuts further enhances market value. This new pecan tree is totally resistant to scab disease prevalent in other varieties in the same orchard. It has an upright, open center growth with a modified central leader providing for good air circulation and sunlight between the leaves which reduces fungus diseases and enhances growth. The growth rate of this tree is very rapid with nut production within four years after grafting. The nuts generally run about forty-two to forty-six to the pound and the cracking percentage is approximately fifty-five percent. Ninety percent of the nuts crack in halves which are of greater commercial value than broken pieces.

1 Drawing Sheet

BACKGROUND AND ORIGIN OF INVENTION

The present invention relates to a new distinct variety of pecan tree discovered growing on my property by me in North Central Nash County, N.C. It is a selected seedling of unknown parentage. The subject seedling will be known commercially as the "Price-Fleming" variety.

SUMMARY OF INVENTION

My attention was directed and devoted to this particular seedling because it annually produced a good crop of high quality nuts, including years of complete crop failure on adjacent improved varieties.

Much travel and effort to inquire of highly regarded pecan authorities did not bring the slightest indication of identification of this pecan. Foremost authorities called upon included: North Carolina State University, Raleigh, N.C.; Fred Voight, PECAN SOUTH Advisory Board, Waycross, Ga.; Ed Abbott, Nurseryman, Monticello, Fla.; and Young Pecan Company, Florence, S.C.

Continued testing, observing and researching over a prolonged period of years have convinced me without a doubt that my "Price-Fleming" seedling is a distinct, new variety which is distinguished from all other pecan varieties of which I am aware. This is evidenced by the following unique combination of commercially valuable features which are outstanding in the "Price-Fleming:"

1. The surface coloration of the full-bodied nut meat is light gold—which is a most desirable color according to the "Pecan Grading Guidelines" as presented in Pecan South, September–October, 1988.

2. The annual productivity is consistently good with the highly flavored, pleasantly textured, light gold meated nuts. The commercial value of these nuts is further enhanced by the very thin shells which separate exceptionally well from the kernals with fifty-five percent fill meat to the whole nut.

3. The tree has a healthy, self-shaping, self-fertile habit which assures good annual nut crops of about ninety to one hundred and ten pound per season. About eighty-five percent of the nuts are released from the hull before it falls.

4. The variety is totally resistant to pecan scab disease as evidenced by its annual production of a good quality nut crop, without the benefit of fungicide for over thirty years.

5. The nut matures early (about ten days before the Stuart) thereby allowing ample marketing time for the Thanksgiving holiday demand for pecans. This feature further increases the value to the grower.

ASEXUAL REPRODUCTION

Asexual reproduction of my new "Price-Fleming" pecan variety by grafting by me in Nash County, N.C., shows that the foregoing characteristics and distinctions survive and are established and transmitted through succeeding propagations as witnessed by Nash County Farm Agent, Jim Stephenson.

DESCRIPTION OF PHOTOGRAPH

The accompanying photograph show typical specimens of the foliage, nuts, and growth pattern of my new "Price-Fleming" pecan variety. Shells of some of the nut specimens are removed to display the kernels. All specimens are depicted as nearly true in shape and/or size as is reasonably possible.

BOTANICAL DESCRIPTION

The following is a detailed description of my new variety, with color terminology in accordance with Pantone Color Guide, 18th Edition, First Printing, 1985–86, a component of the Pantone Library of Color, as based on observations of specimens grown and observed in Nash County, N.C. Although the parentage of the selected Seedling is unknown, the tree and fruit hold their distinguishing characteristics through succeeding propagation by grafting. The new grafts that are now four to seven years old are bearing three to five pounds per tree. The tree is large and vigorous with consistently good productivity annually. The vigorous growth habit produces upright branches with a modified central leader. The wood color is Pantone-478U. This color appears during the second year after grafting. The foliage is abundant, large and heavy. The buds are medium long and slightly pointed. The dates of the first and last pickings in Nash County, N.C. are October 20 and November 15, respectively.

The ripening time is even during the time of harvesting. The quantity is abundant from ninety to one hundred and ten pounds per tree per season. The maturity is medium early with completely free tenacity. The cluster of nuts averages three to five nuts to the cluster. The nuts of this new tree are very large averaging about 2 plus inches in length and 1 inch in diameter. The average number of nuts per pound is forty-two to forty-six. The basal end of the nut is rounded and the point is medium with distinctive high curvature with flat indentations on two sides at the apex end. The shell is very thin, cracks and releases very easily and displays the Pantone 470U color. The kernel is highly flavorful with very firm texture. It is an attractive elongated shape with uneven sutures and spreading at the basal end.

I claim:

1. A new and distinct variety of pecan tree, substantially as herein shown and described, characterized particularly as to novelty by the unique combination of medium-early maturity of high quality, large, tasteful nuts on an annual basis, without the use of fungicide in an area where some pecan varieties are severely affected by pecan scab disease, said nuts having thin shells which separate very easily from the kernel, and a self-fertile and self-shaping habit which assures good annual nut crops even in the absence of any neighboring pecan trees.

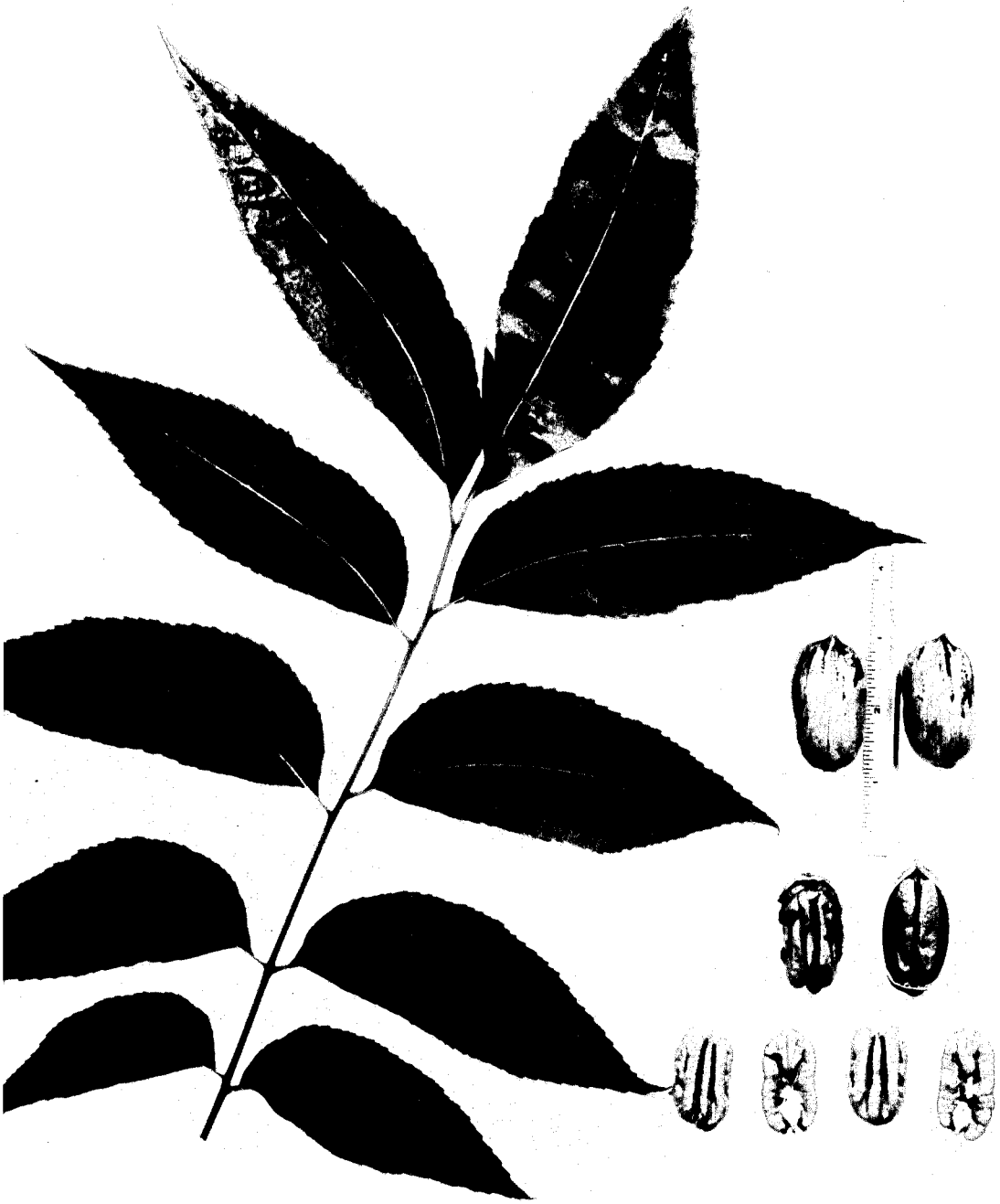

* * * * *